(12) United States Patent
Yano et al.

(10) Patent No.: US 8,329,406 B2
(45) Date of Patent: Dec. 11, 2012

(54) METHOD OF SEPARATING AND DISTINGUISHING WALNUT FROM PECAN NUT

(75) Inventors: Takeo Yano, Nagahama (JP); Yumiko Sakai, Nagahama (JP); Kouji Uchida, Nagahama (JP); Yoshiki Nakao, Nagahama (JP); Kimie Ishihata, Osaka (JP); Shigeru Nakano, Osaka (JP); Toshihiro Yamada, Osaka (JP)

(73) Assignees: Oriental Yeast Co., Ltd., Tokyo (JP); Nissin Foods Holdings Co., Ltd., Osaka-shi (JP)

( * ) Notice: Subject to any disclaimer, the term of this patent is extended or adjusted under 35 U.S.C. 154(b) by 507 days.

(21) Appl. No.: 12/524,735

(22) PCT Filed: Jan. 30, 2008

(86) PCT No.: PCT/JP2008/051454
§ 371 (c)(1),
(2), (4) Date: Jul. 30, 2009

(87) PCT Pub. No.: WO2008/093753
PCT Pub. Date: Aug. 7, 2008

(65) Prior Publication Data
US 2010/0209566 A1    Aug. 19, 2010

(30) Foreign Application Priority Data

Jan. 31, 2007  (JP) ................. 2007-022175

(51) Int. Cl.
*C12Q 1/68*  (2006.01)
*C07H 21/04* (2006.01)
(52) U.S. Cl. ................... 435/6.12; 536/24.33

(58) Field of Classification Search .................. None
See application file for complete search history.

(56) References Cited

FOREIGN PATENT DOCUMENTS

JP    2006 333729    12/2006

OTHER PUBLICATIONS

Takeo Yano, et al., "Detection of Walnut Residues in Processed Foods by Polymerase Chain Reaction", Biosci Biotechnol Biochem. 71(7),pp. 1793-1796, 2007.
Alice M. Stanford, et al., "Phylogeny and Biogeography of Juglans (Juglandaceae) Based on Matk and ITS Sequence Data", American Journal of Botany 87(6), pp. 872-882, 2000.
B. Brezna, et al., "A novel real-time polymerase chain reaction (PCR) method for the detection of walnuts in food", Eur Food Res Technol 223, pp. 373-377, 2006.
Extended European Search Report issued May 7, 2010 in patent application No. 08710648.0.
K. Oravcova, et al., "A Novel Real-Time PCR-Based Method for the Detection of Listeria Monocytogenes in Food", Letters in Applied Microbiology, vol. 45, No. 5, XP008110952, Nov. 2007, pp. 568-573.

*Primary Examiner* — Samuel Woolwine
(74) *Attorney, Agent, or Firm* — Oblon, Spivak, McClelland, Maier & Neustadt, L.L.P.

(57) ABSTRACT

Provided is a method whereby walnut can be simply, rapidly and accurately separated and distinguished from pecan nut. The method involves a PCR method for specifically detecting nuts of the family Juglandaceae and identifying the matK sequence of pecan nut to thereby discriminate walnut and pecan nut from each other optionally using restriction enzymes.

16 Claims, 3 Drawing Sheets

Comparison of the matK genes of the family Juglandaceae

```
                        BfaI            Psp1406I(AclI)
Walnut    :TTATGATAATAAATCTAGTTTACTGATTGTAAAACGTTTAATTACGCGAATGTATCAACAGAATCATTTG
Pecan nut:TTATGATAATAAATATAGTTTACTGATTGTAAAACGTTTAATTACGCGAATGTATCAACAGAATCATTTG
Hickory   :TTATGACAATAAATCCCGTTTACTAATTGTAAAACGGTTAATTACTCGAATGTATCAACAGAATCATTTT
```

Fig. 1

Comparison of the matK genes of the family Juglandaceae

```
                         BfaI              Psp1406I(AclI)
Walnut    :TTATGATAATAAATCTAGTTTACTGATTGTAAACGTTTAATTACGCGAATGTATCAACAGAATCATTTG
Pecan nut:TTATGATAATAAATATAGTTTACTGATTGTAAACGTTTAATTACGCGAATGTATCAACAGAATCATTTG
Hickory   :TTATGACAATAAATCCCGTTTACTAATTGTAAAACGGTTAATTACTCGAATGTATCAACAGAATCATTTT
```

Fig. 2

WAL-F 5'-GAT CTA TAT TGT TGG AAA ATG TAG C-3'   chloroplast maturase (matK) gene / sense WAL-R 5'-GGT TAG AAT CAT TAG TGG AAA TCA G-3'   chloroplast maturase (matK) gene / antisense Walnut 120 bp

```
                      SEQUENCE LISTING

<160> NUMBER OF SEQ ID NOS: 9

<210> SEQ ID NO 1
    <211> LENGTH: 70
    <212> TYPE: DNA
    <213> ORGANISM: Carya illinoensis

<400> SEQUENCE: 1
ttatgataat aaatatagtt tactgattgt aaaacgttta attacgcgaa tgtatcaaca      60
gaatcatttg                                                            70

<210> SEQ ID NO 2
    <211> LENGTH: 25
    <212> TYPE: DNA
    <213> ORGANISM: Artificial Sequence
    <220> FEATURE:
    <223> OTHER INFORMATION: Description of Artificial Sequence: Synthetic
          primer

<400> SEQUENCE: 2
gatctatatt gttggaaaat gtagc                                           25

<210> SEQ ID NO 3
    <211> LENGTH: 25
    <212> TYPE: DNA
    <213> ORGANISM: Artificial Sequence
    <220> FEATURE:
    <223> OTHER INFORMATION: Description of Artificial Sequence: Synthetic
          primer

<400> SEQUENCE: 3
ggttagaatc attagtggaa atcag                                           25

<210> SEQ ID NO 4
    <211> LENGTH: 70
    <212> TYPE: DNA
    <213> ORGANISM: Juglans nigra

<400> SEQUENCE: 4
ttatgataat aaatctagtt tactgattgt aaaacgttta attacgcgaa tgtatcaaca      60
gaatcatttg                                                            70

<210> SEQ ID NO 5
    <211> LENGTH: 70
    <212> TYPE: DNA
```

```
<213> ORGANISM: Carya tomentosa

<400> SEQUENCE: 5
ttatgacaat aaatcccgtt tactaattgt aaaacggtta attactcgaa tgtatcaaca      60
gaatcatttt                                                            70

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggatttctaa ccatcttgtt atcct                                           25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tccagaagat gttaatcgta aatga                                           25

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cggacgagaa taaagataga gt                                              22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttttggggat agagggactt ga                                              22
```

METHOD OF SEPARATING AND DISTINGUISHING WALNUT FROM PECAN NUT

The present application is a 35 U.S.C. §371 National Stage patent application of International patent application PCT/JP2008/051454, filed on Jan. 30, 2008, which claims priority to Japanese patent application JP 2007-022175, filed on Jan. 31, 2007.

TECHNICAL FIELD

The present invention relates to a method of separating and distinguishing walnut from pecan nut. More specifically, the invention relates to a novel and useful method for detecting walnut and pecan nut by using genes in a discriminative manner, simply and accurately.

BACKGROUND OF THE INVENTION

Walnut and pecan nut (also referred to as pecannut) are both edible nuts belonging to the family Juglandaceae and are edible foods. Since patients with the walnut allergen are increasing in Japan regarding walnut, the "walnut" is designated an item recommended to have an allergy label according to the Japan Standard Commodities Classification (the Ministry of Internal Affairs and Communications). Therefore, the development of a method for detecting the walnut allergen is urgently needed.

Meanwhile, pecan nut is not classified in walnut according to the Japan Standard Commodities Classification, although pecan nut is an edible nut belonging to the same family Juglandaceae.

The Japan Standard Commodities Classification
Walnut: caryopsis group→other caryopsis group→walnut
Pecan nut: caryopsis group→other caryopsis group→caryopsis group not classified in other groups.

Because the two are different in their classifications as described above, it is needed to discriminate (distinguish) the two from each other. Although the two are commonly allergic, it is recommended that only walnut should be labeled with such allergen indication. When an allergy occurs, it is now needed to identify the allergy whether the allergen is derived from walnut or pecan nut.

Although the walnut allergen ELISA detection system recently developed was applied, both the allergens of walnut and pecan nut were detected, so that the two could not be detected in a discriminative manner from each other. By the immunochemical method, as described above, it was very difficult to specifically detect walnut alone. As a method for detecting the walnut allergen in a food, the method is very advantageous for patients with the walnut allergy. From the viewpoint of food labels and following the recent increase of the import of pecan nut in Japan, however, the need of a method for detecting walnut and pecan nut in a discriminative manner from each other is further increasing.

An European research team reported a method for specifically detecting walnut by PCR (Polymerase Chain Reaction), recently (non-patent reference 1). However, the method is based on the real-time PCR of a capillary type but is not based on the block-type PCR as a standard method for use in food analyses in Japan. Food analyses by PCR in Japan are mainly done by PCR of the block type with a specific gene as the target. Using the method, methods for detecting wheat, buckwheat, peanut, soybean and kiwifruit (non-patent reference 2) have already been established.

The present inventors newly designed primers capable of specifically detecting edible vegetables with a possibility of the occurrence of food allergy, on the basis of the chloroplast matK (maturase-encoding gene) thereof and then successfully detected walnut in samples by PCR, using these primers (patent reference 1).

The method developed by the inventors is excellent because in addition to the walnut DNA of the genus *Juglans* of the family Juglandaceae of the order Fagales, demon walnut DNA and Persian walnut DNA of the same genus and Sawa-walnut DNA of the genus *Protecaria* of the same family can be detected by the method. However, it is strongly suggested that hickory DNA of the genus *Carya* of the same family of the same order, hazel nut DNA of the genus *Corylus* of the family Betulaceae of the same order, chestnut DNA of the genus *Castanea* of the family Fagaceae of the same order as close species, and DNAs of other biological species including other plants are never detected by the method.

Even in accordance with the invention of the previous application, further, no description is made about the discriminative detection of edible walnut from edible pecan nut of the genus *Carya* of the family Juglandaceae of the order Fagales as a close species. The present invention first achieved successfully the discriminative detection of the two in an accurate and simple manner.

The plants are classified as follows.
Edible walnut: Fagales (order); Juglandaceae (family); *Juglans*
Pecan: Fagales (order); Juglandaceae (family); *Carya*
Hazel: Fagales (order); Betulaceae (family); *Corylus*

The information about the target gene (matK) is as follows. Herein, accession numbers in the GenBank are represented in the parentheses.
Walnut: *Juglansx nigra* (AF118036), *Juglans californica* (AF118027)
Pecan: *Carya tomentosa* (AF118039)
Hazel: *Corylus ubelluna* (AY373445)
Edible pecan: *Carya illinoensis* with no registered gene information
Non-patent reference 1: Eur. Food Res. Technol., 223, 373-377 (2006)
Non-patent reference 2: J. Food Chem., 30, 215-233 (2006)
Patent reference 1: JP-A-2006-333729

DISCLOSURE OF THE INVENTION

Problems that the Invention is to Solve

It is an object of the invention to develop a new method for detecting walnut and pecan nut in a discriminative manner, accurately and simply.

Means for Solving the Problems

So as to attain the object, the inventors made re-investigations on the previous application made by the inventors. In accordance with the previous invention, specifically, PCR primers (SEQ ID Nos. 2 and 3) were designed for specifically detecting nuts of the family Juglandaceae, with attention focused on the gene matK. The specificity of the primer set (FIG. 2) was verified. Consequently, nuts of the family Juglandaceae could be specifically detected by PCR with the primer set. In other words, walnut and pecan nut both could be detected by the PCR (FIG. 3). Furthermore, the detection limits of the purified DNAs of walnut and pecan nut by the PCR with the primers were determined. It was confirmed that the detection sensitivity levels of the two were approximately the same level (0.1 pg (corresponding to 10 ppm) or less by 35 cycles). In conclusion, it was found that walnut and pecan nut could not be discriminated from each other by the method in accordance with the previous invention.

According to the current Japan Standard Commodities Classification, however, pecan nut is not classified in walnut. Hence, it is needed to establish a discriminative detection method of pecan nut and walnut. Therefore, the inventors have made various investigations. Again, the inventors focused their attention to the matK gene in accordance with the previous invention.

It is known that the genus *Carya* of the family Juglandaceae of the order Fagales includes *Carya illinoensis, Carya myristicacformis, Carya pallida, Carya texana, Carya ovata,* and *Carya tomentosa*. However, only *Carya tomentosa* has the known sequence of the matK as the target gene in accordance with the invention. The species for use as an edible nut is *Carya illinoensis* (with unknown matK) while other species are utilized as wood.

As described above, the sequence of the matK gene of *Carya illinoensis* as an edible pecan nut is unknown. Therefore, the inventors analyzed the matK gene of pecan nut to identify the sequence thereof. The nucleotide sequence thereof is shown as SEQ ID NO.1 (FIG. 1). The sequence was compared with the sequence of the matK gene of pecan for use as wood (*C. tomentosa*; hickory). It was revealed that these sequences were different from each other and the sequence differed from the sequence of the walnut matK gene in one base. It was identified that the matK gene of pecan nut was a new sequence unknown previously.

With attention focused to the difference in single one base in the gene regions of walnut and pecan nut to be amplified by PCP. [the base at the 15th position from the 5' side, namely cytosine (C) in walnut, is replaced with adenine (A) in pecan nut], rather, the inventors targeted a new technical issue of discriminating the two from each other on the basis of the single one base.

Based on the information about the identified sequences, the inventors made comparisons and examinations about the sequences of the newly identified matK gene of edible pecan (pecan nut), the known matK gene of walnut, and the matK gene of pecan (Hickory) for use as wood (FIG. 1).

Consequently, the inventors found that due to the substitution of only one base, the BfaI restriction enzyme site present in the gene sequence of walnut was absent in the gene sequence of pecan nut. Additionally, the inventors found that the AcII restriction enzyme site common to walnut and pecan nut, other than the BfaI restriction enzyme site, was absent in the pecan species for use as wood. Based on the aforementioned discoveries, the inventors made investigations whether or not walnut and pecan nut could be discriminated from each other using the restriction enzymes. Thus, the inventors verified that the discrimination thereof was possible.

From the standpoint that walnut and pecan nut might possibly be detected in a discriminative manner by using the restriction enzymes BfaI and AcII, specifically, the inventors cleaved amplification products of walnut DNA and amplification products of pecan nut with the restriction enzymes so as to verify the possibility. Consequently, the inventors identified that an AcII site present commonly in the walnut and pecan nut gene regions amplified by PCR and that the BfaI restriction enzyme site present in the walnut gene region amplified by PCR was absent in the pecan nut gene region amplified by PCR (FIG. 4).

As apparently shown on the agarose gel electrophoresis charts, in other words, it was confirmed that two bands of walnut-specific fragments (40 bp, 80 bp) through cleavage after BfaI treatment were observed in the walnut with the BfaI site, while one 120-bp band was singly observed in pecan nut without the site even after the BfaI treatment, because pecan nut was never cleaved.

This demonstrates that pecan nut and walnut can be discriminated from each other on the basis of one base difference in the matK genes, in a simple and accurate manner by treating the individual PCR products with the restriction enzyme BfaI and comparing the electrophoresis patterns of the treated products, without any direct comparison of the sequences of the genes. Thus, the invention has finally been achieved on the basis of these new and useful findings and subsequent investigations.

Advantages of the Invention

Following the increase of patients with the walnut allergen and the increase of the import of pecan nut as an edible nut of the family Juglandaceae, the development of a method for discriminating walnut and pecan nut from each other has been urgently needed. With attention focused on the chloroplast matK gene with an apparent gene sequence, we developed PCR for specifically detecting nuts of the family Juglandaceae and further demonstrated the sequence of pecan nut matK so as to discriminate walnut and pecan nut from each other. Hence, we established a method for discriminating walnut and pecan nut from each other, using the restriction enzymes.

BEST MODE FOR CARRYING OUT THE INVENTION

For implementing the invention, it is on by necessary to examine one base at the 15th position from the 5' side in the nucleotide sequence of SEQ ID NO. 1 (the sequence is shown in the middle column (pecan nut) in FIG. 1) of the matK gene of the family Juglandaceae. Specifically, the matK gene may be isolated from each sample to directly determine whether or not the base-15 is A or C. Otherwise, the aforementioned procedures may be done by utilizing the SNPs analysis technique, for example the SMAP method (Riken).

In accordance with the invention, additionally, the two can accurately be detected in a discriminative manner simply and rapidly and additionally even accurately by PCR, without any direct examination of the sequences of the matK genes themselves.

As the primers, DNA represented by the nucleotide sequence of SEQ ID NO.2 is used as a sense primer, while DNA represented by the nucleotide sequence of SEQ ID NO.3 is used as an antisense primer (FIG. 2). These primers were developed in accordance with the previous invention by the inventors for walnut. The primers are characteristically used even for pecan nut.

Using these DNAs as primers and the genome DNA extracted from a sample as template, PCR is carried out. PCR may be done by general methods. Using for example Gene Amp (registered trademark) PCR system 9700 (Applied Biosystems), PCR may be done. The conditions for the amplification reaction are as follows: pre-incubation at 95° C. for 10 minutes and 35 amplification cycles, each cycle comprising retaining at 95° C. for 0.5 minute, annealing at 64° C. for 0.5 minute, extention at 72° C. for 0.5 minute and final extension at 72° C. for 7 minutes, are carried out.

The nucleotide sequences of the PCR amplification products thus obtained are determined to examine the specific one base in a similar manner as in the case of the matK gene as described above, so that the two can be detected in a discriminative manner. The two can be detected in a discriminative manner by treating the PCR amplification products with a restriction enzyme BfaI and then examining the resulting PCR fragments by electrophoresis, with no need of the examination of the sequences of the PCR products.

EXAMPLES

Examples of the invention are described hereinbelow. However, the invention is not limited by these Examples.

Example 1

(1) Using primers comprising DNAs individually represented by the nucleotide sequences of SEQ ID NO.2 (the upper column in FIG. 2) and SEQ ID NO.3 (the lower column in FIG. 2) and the genome DNAs extracted from individual samples as templates, PCR was done. PCR was carried out by routine methods, for example under the conditions described above.

After termination of PCR, the PCR amplification products were separated by agarose gel electrophoresis; the gels after separation were stained with ethidium bromide, to visually observe the amplification products under UV irradiation, to determine the presence or absence of the amplification products. As molecular weight markers, 100-bp DNA Ladder (New England BioLabs Inc., USA) was used. The results of such PCR are shown in FIG. 3. Consequently, both pecan nut (lane 7) and walnut (lane 8) showed the same pattern, which indicates that the two could not be discriminated from each other by simple electrophoresis.

(2) Therefore, it was intended to determine the sequences of the PCR products. The method for determining the sequences is as follows. Because the sequence of the matK gene of pecan nut (*Carya illinoensis*) was unknown, the sequence was identified by the standard PCR cloning technique.

Since the sequence of the matK gene of pecan nut (*Carya illinoensis*) was unknown, the nucleotide sequence of the PCR product was determined. The nucleotide sequence was determined by the TA cloning technique (Marchuk, D., Drumm, M., Saulino, A., and Collins, F. S., Nucleic Acids Res., 19, 1154, 1991) as a routine method.

Concretely, in the light of the known nucleotide sequence of the walnut matK (Genbank accession #AF118027), a primer set for the outer region of the walnut primers (the sense primer: the nucleotide-378 to nucleotide-402 sequence in the walnut AF118027, namely GGATTTCTAACCATCTTGT-TATCCT (SEQ ID NO: 6); the antisense primer: the nucleotide-1295 to nucleotide-1319 sequence in the walnut AF118027, namely TCCAGAAGATGTTAATCG-TAAATGA (SEQ ID NO: 7)); was designed. Using the primer set and the pecan nut DNA as template, PCR was done. The resulting PCR product was cloned, using a TA cloning kit TOPO TA Cloning (registered trademark of Invitrogen). The PCR product was integrated in a cloning vector attached to the kit, namely pCRII-TOPO vector (registered trademark), for transformation of a host *Escherichia coli* (JM109) with the cloning vector by a routine method.

Since the ampicillin-resistant gene is integrated in the vector, only the host introduced with the vector can be selected via culturing on an LB plate containing ampicillin. 10 colonies were selected from the resulting colonies to determine whether or not the PCR product gene was integrated in the vector by the colony PCR using the primer set. It was confirmed that the PCR product gene was integrated in all of the selected colonies.

Further, three colonies were selected from those 10 colonies, to purify the vector plasmid with the PCR product integrated therein to determine the nucleotide sequence by a routine method using the primers (M13 Forward (−20) primer and M13 Reverse primer) previously designed for nucleotide sequencing of the cloning vector. It was verified that all of the three clones had the same nucleotide sequence.

FIG. 1 shows the determined nucleotide sequence of a region of the pecan nut matK gene, which was amplified with the walnut primers. DNA was extracted from the two pecan nut products commercially available for edible use, namely pecan nut produced in Arizona, USA (Profood Corporation) and Western Schley species (Kitchen Garden, Confectionary Material Net Store Pateris) produced in USA/Australia, to confirm the nucleotide sequences thereof by the same method. The nucleotide sequences of the two products were identical to the nucleotide sequence of pecan nut as shown in FIG. 1. In the figure, Walnut shows walnut; Pecan nut shows pecan nut; and Hickory shows hickory. The sequence of pecan nut is a novel sequence conventionally never known and the nucleotide sequence thereof is shown as SEQ ID NO.1.

It is shown on these sequence comparisons that these nucleotide sequences for walnut and pecan nut differ from each other in the base-15 but it has never been expected that the two could be discriminated from each other on the basis of the difference in one single base alone. As described below, it was verified that the difference in single one base could be detected in a discriminative manner through restriction enzyme treatments. It is very innovative to enable the discrimination of the two on the basis of the difference in only one base, extremely characteristically. Thus, the invention is highly patentable.

So as to discriminate the two from each other, accordingly, the sequences of the matK genes should be compared together, to determine whether the base-15 is A or C to discriminate the two from each other. Otherwise, the discrimination can be done by the SMAP method (Riken) and the like. However, the inventors developed a far simpler method.

(3) Walnut and pecan nut were discriminated from each other by restriction enzyme treatments of PCR fragments Specifically, samples 1, 3, 5 and 7 were walnut PCR fragments (50 ng/ml), while samples 2, 4, 6 and 8 were pecan nut PCR fragments (50 ng/ml). The composition for the reaction was 2 μl in volume of DNA and 1 μl of an enzyme volume (AclI: 3,000 U/ml, BfaI: 5,000 U/ml) in total of 20 μl. The reaction was done by incubation at 37° C. for 3.5 hours. The products from the restriction enzyme treatments were subjected to electrophoresis on 2.5% agarose gel (3 μl).

FIG. 4 shows charts of the electrophoresis. As apparently shown in the results of the charts, walnut has a different pattern (lanes 5 and 7) from that of pecan nut (lane 6) as visually observed instantly, where a pattern of two walnut-specific fragments on cleavage with BfaI is shown on the lanes 5 and 7.

The results agree well with the expected fragment lengths. In other words, the two involved a 120-bp fragment in case of no cleavage while incase of cleavage with AclI, the two involved 59-bp and 61-bp fragments; incase of cleavage with BfaI, walnut involved 40-bp and 80-bp fragments and pecan nut involved a 120-bp fragment; incase of cleavage with AclI and BfaI, walnut involved 19-bp, 40-bp and 61-bp fragments while pecan nut involved 59-bp and 61-bp fragments. Hence, these fragment lengths agreed well with the expected fragment lengths.

Therefore, pecan nut can be detected in a discriminated manner from walnut, simply, rapidly and accurately by electrophoresis treatment of the BfaI-treated products of the PCR products.

BRIEF DESCRIPTION OF THE DRAWINGS

FIG. 1 The comparison of the sequences of the matK genes of the family Juglandaceae is shown, where the sequence of SEQ ID No.1 is shown in the middle column (pecan nut). Walnut sequence disclosed as SEQ ID NO: 4. Hickory sequence disclosed as SEQ ID NO: 5.

FIG. 2 Primers are shown. The sense primer (SEQ ID NO.2) is shown in the upper column. The antisense primer (SEQ ID NO:3) is shown in the lower column.

Photos in place of drawings depicting the electrophoresis patterns of the PCR amplification products of the nuts. In the figure, the upper column shows the results with the standard primers for plants (corresponding to the control) while the lower column shows the results with the primers for walnut. Herein, CP03-5' and CP03-3' depict the primers for plant DNA detection, where the sequence of the former (F-primer) is CGGACGAGAATAAAGATAGAGT (SEQ ID NO: 8); and the sequence of the latter (R-primer) is TTTTGGGGATA-GAGGGACTTGA (SEQ ID NO: 9). The sequences of these primers and the PCR conditions therefor are described in the notice from the Pharmaceutical and Food Safety Bureau, the Ministry of Health, Labor and Welfare, namely "Test method of foods containing allergic substances" (Shoku-an No. 0622003).

Figure 3:
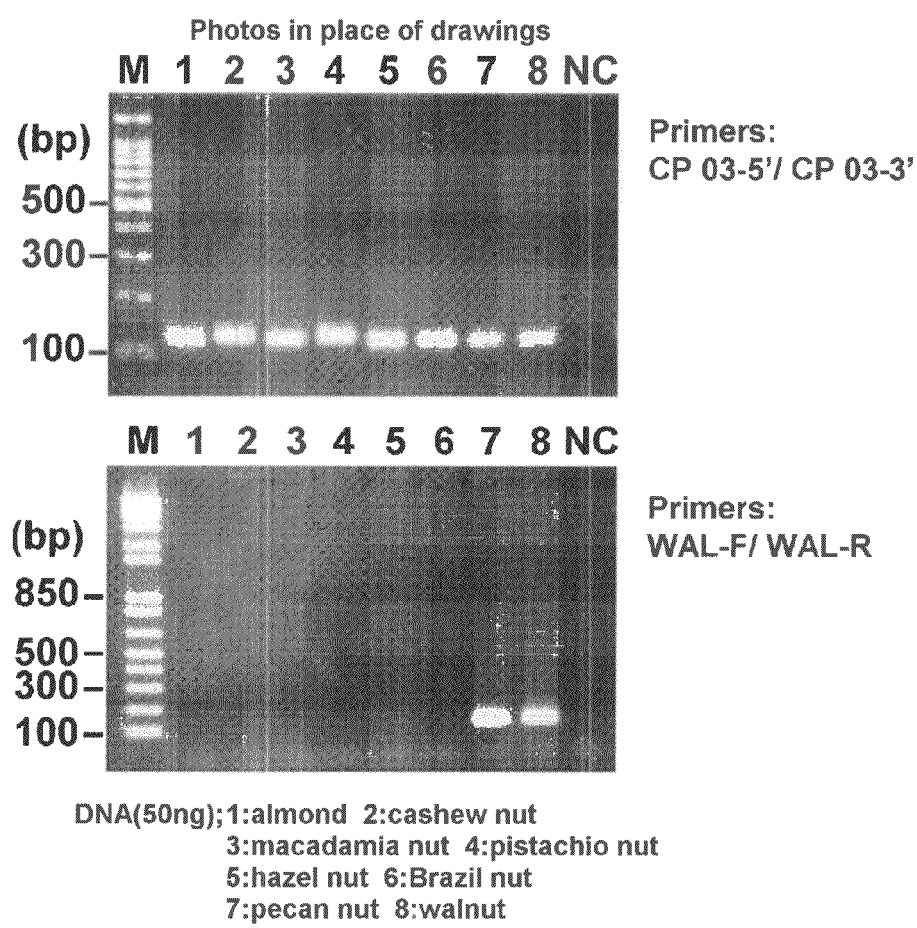
Figure 4:
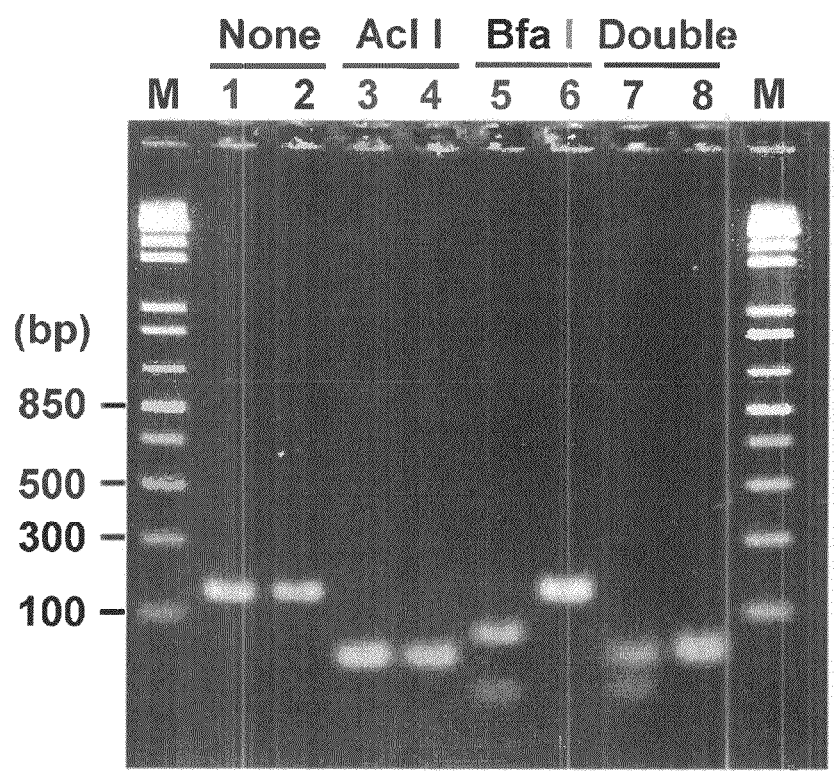

FIG. 4 Photos in place of drawings depicting the electrophoresis patterns for discriminating PCR fragments by restriction enzyme treatments. In the figure, Walnut shows walnut; Pecan nut shows pecan nut.

The invention claimed is:

1. A method for discriminating between a walnut and pecan nut, the method comprising:

amplifying a sample by the polymerase chain reaction (PCR) with a first primer comprising SEQ ID NO:2 and a second primer comprising SEQ ID NO:3 to obtain an amplified product; and determining the presence of a walnut or a pecan nut based on the amplified product, wherein, if the amplified product comprises an adenine at position 15 of SEQ ID NO:1, then the sample is from a pecan nut, and, if the amplified product comprises a cytosine at position 15 of SEQ ID NO:1, then the sample is from a walnut.

2. The method of claim 1, wherein the first primer consists of SEQ ID NO:2 and the second primer consists of SEQ ID NO:3.

3. The method of claim 1 wherein the determining comprises treating the amplified product with a restriction enzyme BfaI;

subjecting the treated amplified product to electrophoresis; and then determining a difference in an electrophoresis pattern.

4. The method of claim 1, further comprising:

treating the amplified product with a restriction enzyme BfaI.

5. The method of claim 1, wherein the PCR is carried out for 35 cycles.

6. The method of claim 1, wherein the PCR is carried out at a temperature of 95° C. for denaturing, 64° C. for annealing, and 72° C. for extension.

7. The method of claim 1, wherein PCR amplification is carried out after preincubating at 95° C.

8. The method of claim 1, wherein PCR amplification is carried out after preincubating for 10 minutes.

9. The method of claim 2, further comprising:
cleaving the amplified PCR products with a restriction enzyme BfaI.

10. The method of claim 9, further comprising:
after the cleaving, submitting the amplified PCR products to electrophoresis.

11. The method of claim 2, wherein the PCR is carried out at a temperature of 95° C. for denaturing, 64° C. for annealing, and 72° C. for extension.

12. The method of claim 2, wherein the PCR is carried out for 35 cycles.

13. The method of claim 10, wherein electrophoresis is performed in an agarose gel.

14. The method of claim 2, wherein PCR amplification is carried out after preincubating at 95° C.

15. The method of claim 2, wherein PCR amplification is carried out after preincubating for 10 minutes.

16. The method of claim 3, wherein electrophoresis is performed in an agarose gel.

* * * * *